(12) United States Patent
Kuck et al.

(10) Patent No.: US 9,149,320 B2
(45) Date of Patent: Oct. 6, 2015

(54) ISOLATION OF PULMONARY VEIN

(75) Inventors: Karl Heinz Kuck, Hamburg (DE); Julian Chun, Hamburg (DE); Feifan Ouyang, Hamburg (DE); Nicolas Coulombe, Montréal (CA); Jean-Luc Pageard, Montréal (CA); Randy Jordan, Calgary (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 1892 days.

(21) Appl. No.: 12/363,832

(22) Filed: Feb. 2, 2009

(65) Prior Publication Data

US 2010/0198203 A1 Aug. 5, 2010

(51) Int. Cl.
*A61B 18/02* (2006.01)
*A61B 18/00* (2006.01)
*A61M 25/10* (2013.01)

(52) U.S. Cl.
CPC ......... *A61B 18/02* (2013.01); *A61B 2018/0022* (2013.01); *A61B 2018/0212* (2013.01); *A61B 2018/0262* (2013.01); *A61M 2025/1097* (2013.01)

(58) Field of Classification Search
CPC ........... A61B 18/02; A61B 2018/0022; A61B 2018/0212; A61B 2018/0262; A61B 2018/00577; A61B 2018/0268; A61B 2018/00011; A61B 2018/00005; A61M 2025/1097
USPC ........ 606/20, 21, 22, 192–200; 604/194, 914, 604/509, 96.01–109, 915–921
See application file for complete search history.

(56) References Cited

U.S. PATENT DOCUMENTS

| | | | | |
|---|---|---|---|---|
| 4,733,669 A | * | 3/1988 | Segal | 600/585 |
| 5,104,859 A | * | 4/1992 | Sollevi | 514/46 |
| 5,318,535 A | * | 6/1994 | Miraki | 604/103.1 |
| 5,342,306 A | * | 8/1994 | Don Michael | 604/101.04 |
| 6,077,256 A | * | 6/2000 | Mann | 604/500 |
| 6,673,039 B1 | * | 1/2004 | Bridges et al. | 604/96.01 |
| 6,699,231 B1 | * | 3/2004 | Sterman et al. | 604/509 |
| 6,912,419 B2 | * | 6/2005 | Hill et al. | 607/9 |
| 7,220,257 B1 | * | 5/2007 | Lafontaine | 606/21 |
| 7,532,938 B2 | * | 5/2009 | Machado et al. | 607/116 |
| 2001/0003795 A1 | * | 6/2001 | Suresh et al. | 604/96.01 |
| 2003/0187428 A1 | * | 10/2003 | Lane et al. | 606/21 |
| 2004/0158276 A1 | * | 8/2004 | Barbut et al. | 606/200 |
| 2006/0224153 A1 | * | 10/2006 | Fischell et al. | 606/41 |
| 2009/0177090 A1 | * | 7/2009 | Grunwald et al. | 600/454 |
| 2013/0237817 A1 | * | 9/2013 | Mihaljevic et al. | 600/435 |

OTHER PUBLICATIONS

Richard Ian Ogilvie, MD and Danuta Zborowska-Sluis, MD, "Effect of Chronic Rapid Ventricular Pacing on Total Vascular Capicatance." Apr. 1992. Circulation. vol. 85, No. 4. pp. 1524-1530.*
Ogilvie, R.I. And Zborowska-Sluis, D. "Effect of chronic rapid ventricular pacing on total vascular capacitance." 1992, Circulation. vol. 85, pp. 1524-1530.*
Daehnert, I., Rotzsch, C., Wiener, M. and Schneider, P. "Rapid right ventricular pacing is an alternative to adenosine in catheter interventional procedures for congenital heart disease" 2004, Heart. vol. 90, pp. 1047-1050.*

* cited by examiner

*Primary Examiner* — Nicholas Lucchesi
*Assistant Examiner* — Weng Lee
(74) *Attorney, Agent, or Firm* — Christopher & Weisberg, P.A.

(57) ABSTRACT

The present invention advantageously provides a method and system for the improved isolation and corresponding treatment of tissue targeted for cryogenic or other thermal therapy to increase the thermal efficacy and thermal efficiency of the treatment. In particular, the present invention provides methods and systems for improved thermal treatment of target tissue, such as a pulmonary vein and/or regions of the left atrium by reducing the resistive forces and/or increased thermal energy experienced from blood flow exiting the pulmonary vein into the left atrium during treatment.

7 Claims, 8 Drawing Sheets

ISOLATION OF PULMONARY VEIN

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to medical devices and methods of use, and in particular, to a method and system for thermally treating cardiac tissue.

BACKGROUND OF THE INVENTION

Minimally invasive surgical techniques are known for performing medical procedures within the cardio-vascular system. Exemplary known procedures include the steps of passing a small diameter, highly-flexible catheter through one or more blood vessels and into the heart. When positioned as desired, additional features of the catheter are used, in conjunction with associated equipment, to perform all or a portion of a medical treatment, such as vessel occlusion, tissue biopsy, or tissue ablation, among others. Almost always, these procedures are performed while the heart is beating and blood is flowing. Not surprisingly, even though visualization and positioning aids are adequate for general placement of the device, maintaining the device in a selected position and orientation can be difficult as the tissue moves and blood flows, especially during a procedure that must be done relatively quickly.

One such minimally-invasive technique includes the use of catheter based devices, employing the flow of cryogenic working fluids therein, to selectively freeze, or "cold-treat", targeted tissues within the body. Catheter based devices are desirable for various medical and surgical applications in that they are relatively non-invasive and allow for precise treatment of localized discrete tissues that are otherwise inaccessible. Catheters may be easily inserted and navigated through the blood vessels and arteries, allowing non-invasive access to areas of the body with relatively little trauma.

A cryogenic catheter-based ablation system uses the energy transfer derived from thermodynamic changes occurring in the flow of a cryogen therethrough to create a net transfer of heat flow from the target tissue to the device, typically achieved by cooling a portion of the device to very low temperature through conductive and convective heat transfer between the cryogen and target tissue. The quality and magnitude of heat transfer is regulated by the device configuration and control of the cryogen flow regime within the device.

A number of medical conditions may be treated using these ablative techniques or devices. For example, atrial fibrillation is a medical condition resulting from abnormal electrical activity within the heart. This abnormal activity may occur at regions of the heart including the sino-atrial (SA) node, the atrioventricular (AV) node, the bundle of His, or within other areas of cardiac tissue. Moreover, atrial fibrillation may be caused by abnormal activity within an isolated focal center within the heart. These foci can originate within a pulmonary vein, and particularly the superior pulmonary veins. Atrial fibrillation may be treatable by ablation of the abnormal tissue within the left atrium and/or the pulmonary vein. In particular, minimally invasive techniques, such as those described above, use ablation catheters to target the pulmonary vein in order to ablate any identified foci having abnormal electrical activity.

For atrial fibrillation, a cryogenic device is generally positioned at the ostium of a pulmonary vein ("PV") such that any blood flow exiting the PV into the left atrium ("LA") is completely blocked. At this position the cooling of the balloon system may be activated for a sufficient duration to create a desired lesion at the PV-LA junction. During the operation of a medical device, such as a cryogenic catheter, in a therapeutic procedure to treat a blood vessel, the heart or other body organ, its desirable to establish a stable and uniform contact between the thermally-transmissive (i.e., "cold") region of the cryogenic device and the tissue to be treated (e.g., ablated). In those instances where the contact between the thermally-transmissive region of the cryogenic device and the tissue to be treated is non-uniform or instable, the resulting ablation or lesion may be less than optimal.

Difficulties arise in establishing or maintaining optimal positioning and contact between the treatment device and the target tissue. In particular, potential limitations of the cryogenic (or other thermal treatment) technique include the duration of time to create a transmural lesion, and the negative effects the high blood flow from the PV's has on the thermal efficacy and efficiency of the treatment. For example, the blood flow from the PV's may push the ablation device out of the PV since the blood flow is directed from the PV's into the LA in the opposite direction of the balloon placement, which is positioned at the ostium of the PV. Further, the blood contacting and/or flowing past the treatment device or ablation catheter has a temperature of 37° C., which raises the temperature of the treatment device, thereby reducing the thermal efficacy and efficiency of the device when attempting to achieve low temperatures rapidly.

In view of the above, it is desirable to provide for the improved isolation and corresponding treatment of tissue targeted for cryogenic or other thermal therapy to increase the thermal efficacy and thermal efficiency of the treatment.

SUMMARY OF THE INVENTION

The present invention advantageously provides a method and system for the improved isolation and corresponding treatment of tissue targeted for cryogenic or other thermal therapy to increase the thermal efficacy and thermal efficiency of the treatment.

In particular the present invention includes a method for treating cardiac tissue, including substantially occluding at least a portion of a pulmonary artery; and thermally treating at least a portion of a pulmonary vein, where thermally treating may be accomplished at least in part by cryogenically cooling the portion of the pulmonary vein; where substantially occluding at least a portion of the pulmonary artery may be accomplished with a first medical device, and where thermally treating at least a portion of the pulmonary vein may be accomplished with a second medical device. Further, at least one of the first and second medical devices may include a balloon. For example, the first medical device may include a balloon, and the method may include providing a bypass flow path from a region distally of the balloon to a region proximally of the balloon, where the balloon surrounds at least a portion of the bypass path.

The present invention also provides a method for treating cardiac tissue, including positioning an expandable element in proximity to a pulmonary vein; providing a bypass flow path from a region distally of the expandable element to a region proximally of the expandable element, where the expandable element surrounds at least a portion of the bypass path; and thermally treating at least a portion of the pulmonary vein. Thermally treating the portion of the pulmonary vein may include injecting a coolant into the expandable element. The method may include providing a fluid control element in fluid communication with the bypass flow path and selectively operating the fluid control element to modify fluid flow through the bypass flow path.

The present invention further provides a method for treating cardiac tissue, including inducing a reduction in cardiac output; and thermally treating at least a portion of a pulmonary vein. Inducing a reduction in cardiac output may include delivering a pharmacological compound to the cardiac tissue and/or applying an electrical signal to the cardiac tissue. Inducing a reduction in cardiac output may include right ventricular pacing at a rate of approximately 200 beats per minute. Thermally treating the portion of the pulmonary vein may be accomplished at least in part by cryogenically cooling the portion of the pulmonary vein.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

The present invention advantageously provides a method and system for the improved isolation and corresponding treatment of tissue targeted for cryogenic or other thermal therapy to increase the thermal efficacy and thermal efficiency of the treatment. In particular, the present invention provides methods and systems for improved thermal treatment of target tissue, such as a pulmonary vein and/or regions of the left atrium by reducing the resistive forces and/or increased thermal energy experienced from blood flow exiting the pulmonary vein into the left atrium during treatment.

Figure 1:
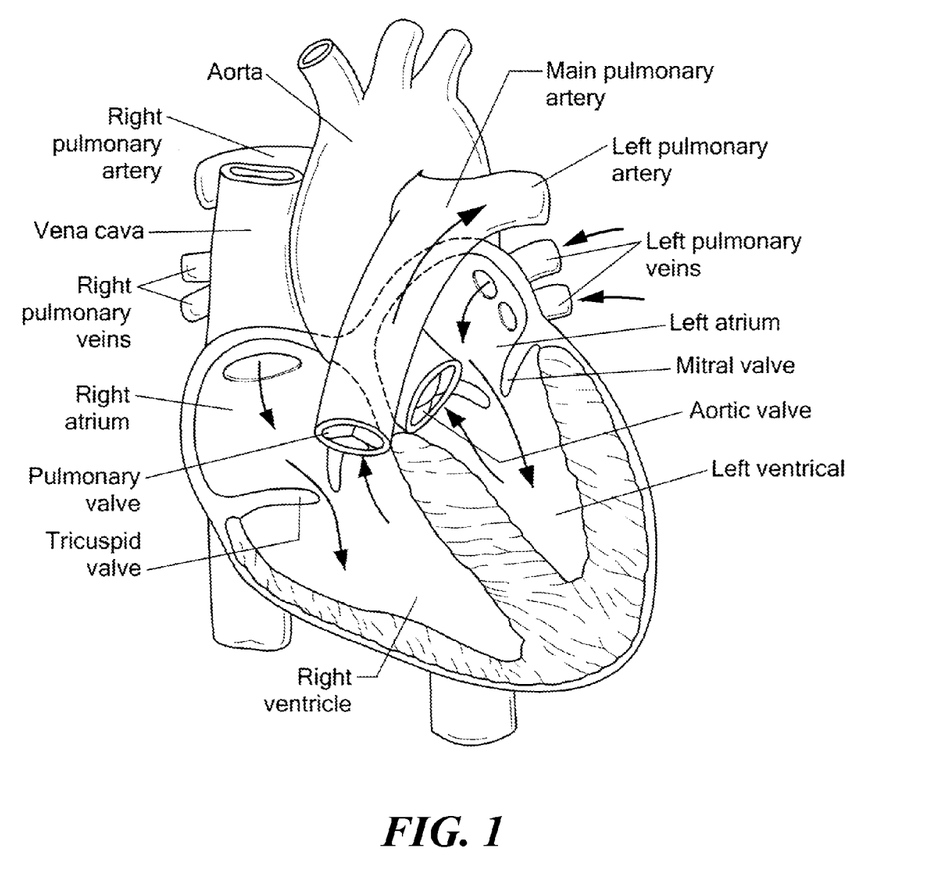
FIG. 1 is a cross-sectional illustration of a heart.

Prior to describing the present invention, an understanding of the circulation of blood through the heart is provided. Referring now to FIG. 1, a cross-sectional view of a heart is illustrated. In particular, the heart includes a right atrium, a right ventricle, a left atrium and a left ventricle. During cardiac contractions, blood enters the heart through two large veins, the inferior and superior vena cava, emptying oxygen-poor blood from the body into the right atrium. Blood flows from the right atrium into the right ventricle through the tricuspid valve. From the right ventricle, blood flows into the pulmonary artery and directed towards the lungs. Once oxygenated in the lungs, blood flow proceeds into the pulmonary vein for passage into the left atrium. From the left atrium, blood proceeds into the left ventricle through the mitral valve, and proceeds into the aorta for circulation through the body.

As discussed above, particular cardiac treatments involving thermal therapy, such as the application of cryogenic energy or cooling, are used to ablate problematic regions of tissue. These problematic areas may be contributing to electrophysiological anomalies in the heart, including arrhythmias such as atrial fibrillation, tachycardia, or other contractual maladies. To treat these targeted tissue areas, one or more medical devices may be directed towards the left atrium for the subsequent delivery of thermal energy or therapy.

Figure 2:
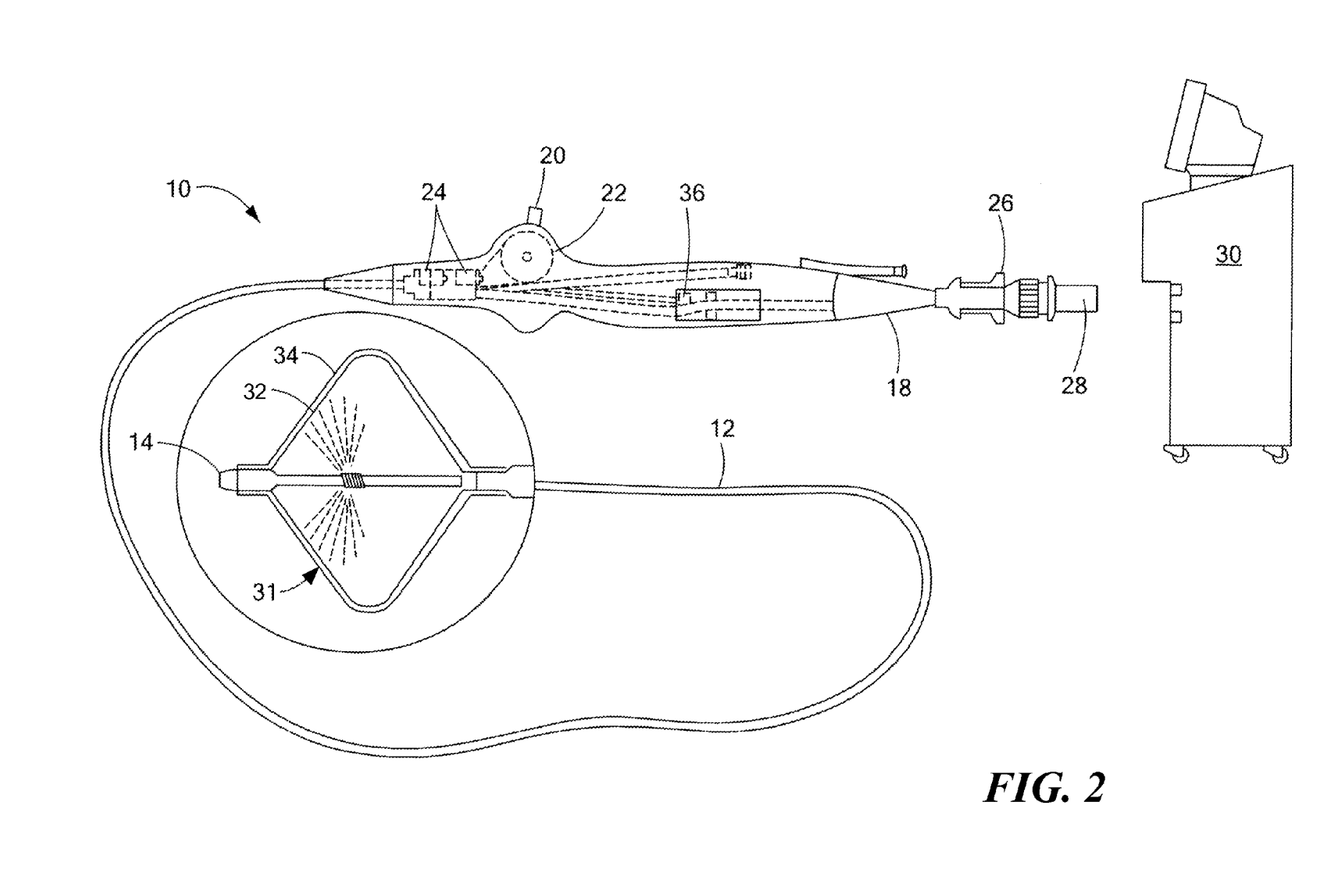
FIG. 2 is an illustration of an embodiment of a medical device constructed in accordance with the principles of the present invention.

Now referring to FIG. 2, an exemplary embodiment of a medical device system constructed in accordance with the principles of the present invention is shown. In particular, FIG. 2 illustrates an exemplary system suitable for performing cryogenic ablation. The system includes a medical device 10, such as an elongate highly flexible ablation catheter that is suitable for passage through the vasculature. The ablation catheter includes a catheter body 12 having a distal end 14 with an ablation element 16 at or proximal to the distal end 14. The distal end 14 and the ablation element 16 are shown magnified and are described in greater detail below. The ablation catheter has a proximal end that is mated to a handle 18 that can include an element such as a lever or knob 20 for manipulating the catheter body and the ablation element. In the exemplary embodiment, a pull wire having a proximal end and a distal end has its distal end is anchored to the catheter at or near the distal end. The proximal end of the pull wire is anchored to an element such as a cam 22 in communication with and responsive to the lever 20. The handle 18 can further include circuitry 24 for identification and/or use in controlling of the ablation catheter or another component of the system.

Continuing to refer to FIG. 2, the handle 18 can also include connectors that are matable directly to a cryogenic fluid supply/exhaust and control unit or indirectly by way of one or more umbilicals. In the system illustrated, the handle is provided with a first connector 26 that is matable with a co-axial fluid umbilical (not shown) and a second connector 28 that is matable with an electrical umbilical (not shown) that can further include an accessory box (not shown). In the exemplary system the fluid supply and exhaust, as well as various control mechanisms for the system are housed in a single console 30. In addition to providing an exhaust function for the ablation catheter fluid supply, the console 30 can also recover and/or recirculate the cooling fluid. The handle may be provided with a fitting for receiving a guide wire (not shown) that is passed into a guide wire lumen.

Still referring to FIG. 2, the ablation element 31 is shown as a double balloon, wherein an inner balloon 32 is contained by an outer balloon 34. A coolant supply tube in fluid communication with the coolant supply in the console 30 is provided to release coolant from one or more openings in the tube within the inner balloon in response to console commands and other control input. A vacuum pump in the console creates a low pressure environment in one or more lumens within the catheter body so that coolant is drawn into the lumen(s), away from the inner balloon, and toward the proximal end of the catheter body. The vacuum pump may also be in fluid communication with the interface of the inner and the outer balloons so that any fluid that leaks from the inner balloon is contained and aspirated.

The handle 18 may include one or more pressure sensors 36 to monitor the fluid pressure within one or both of the balloons, blood detection devices and pressure relief valves. When coolant is released into the inner balloon, the inner and the outer balloon expand to present an ablation surface, wherein the temperature of the ablation surface is determined at least in part by the material properties of the specific coolant selected for use, such as nitrous oxide, along with the operational characteristics of the system, such as coolant pressure, flow rate, or the like.

Figure 3:
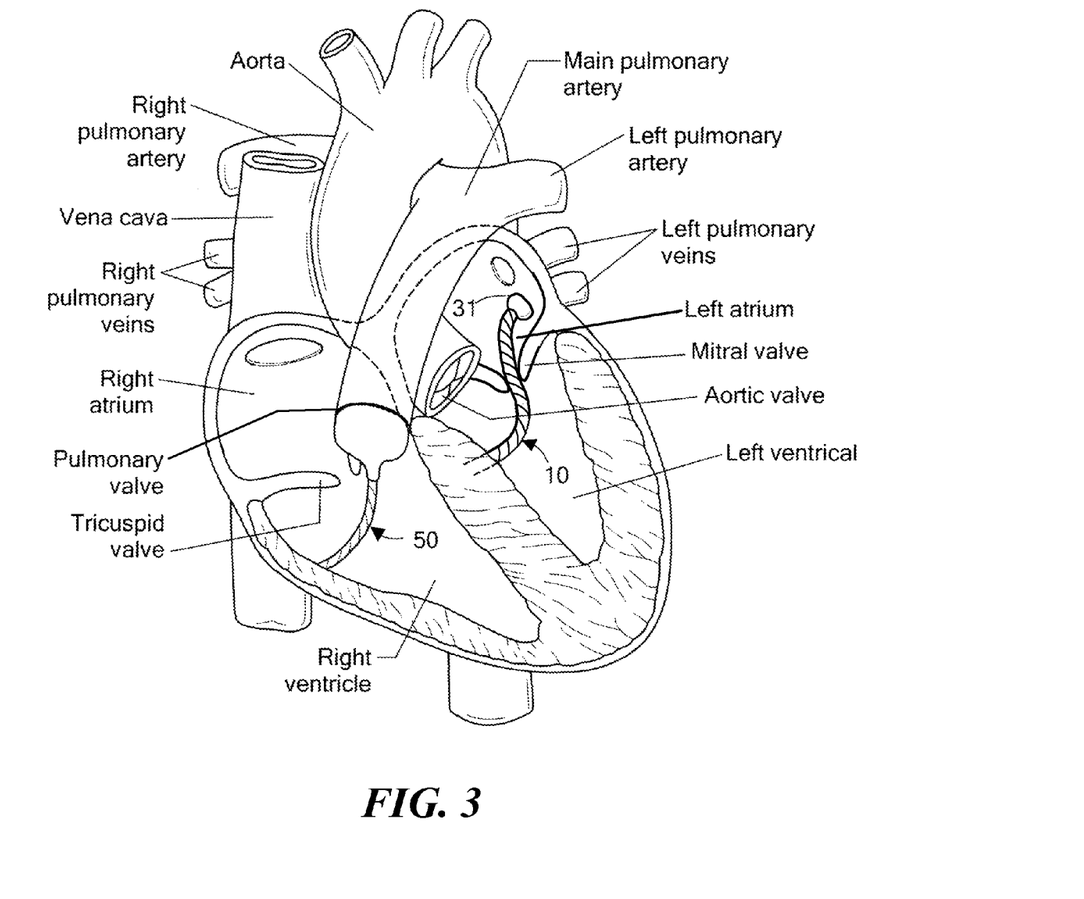
FIG. 3 is an illustration of an embodiment of a treatment technique in accordance with the principles of the present invention.

Now referring to FIG. 3, the medical device 10 may be positioned in the left atrium, and in particular, in proximity to a pulmonary vein for thermal treatment of the ostium of the pulmonary vein-left atrium intersection. For example, a sheath or guide catheter may be inserted into a blood vessel that leads to the right atrium of the heart and passed through an opening created in the septum that separates the right and left atria into the left atrium. Once in the left atrium, the ablation element 31 of the medical device 10 may be positioned to abut, contact, or substantially occlude the pulmonary vein opening and the ostium of the left atrium for treatment, such as the application of cryogenic cooling.

As discussed, secure placement and contact of the medical device against the ostium may be frustrated by blood flowing out of the pulmonary vein and into the left atrium. Further, effective and efficient cooling of the target tissue may also be hampered due to the thermal interaction and warming effect the flowing blood may have on the medical device. As such, a secondary medical device 50 may be positioned within at least a portion of the pulmonary artery to occlude blood flow exiting the right ventricle and into the pulmonary artery.

For example, the substantial occlusion of the pulmonary artery may be achieved through the positioning and use of secondary vasculature occlusion devices, such as a balloon catheter, a clamping device, or other vascular obstructing mechanisms as known in the art. The secondary balloon catheter may be directed through the vasculature and into a portion of the pulmonary artery and/or right ventricle. The secondary balloon catheter may then be inflated to substantially occlude the pulmonary artery, thereby significantly reducing the flow of blood from the right ventricle into the pulmonary artery.

Because the pulmonary artery directs blood flow into the lungs and subsequently into the pulmonary vein, the substantial occlusion of the pulmonary artery may significantly reduce the blood flow exiting the pulmonary vein and into the left atrium. This blood flow reduction in the pulmonary vein thereby reduces the likelihood of positioning difficulties and/or thermal treatment inefficiencies that would otherwise occur from the unobstructed blood flow and its interaction with the ablation element 31 of the medical device 10.

Once the desired contact and positioning of the ablation element 31 or the medical device 10 has been established, thermal treatment may be applied to the contacted tissue. For example, should the device include one or more balloons, the balloons may be inflated by the circulation of a cryogenic coolant therethrough, resulting in the rapid cooling of the tissue contacting the balloons of the ablation element. The cryogenic application may be maintained for a predetermined amount of time in order to produce the desired result or lesion.

Upon completion of the treatment, detection of electrophysiological activity may be performed via a multipolar electrode catheter to determine the effectiveness of the treatment.

Figure 4:
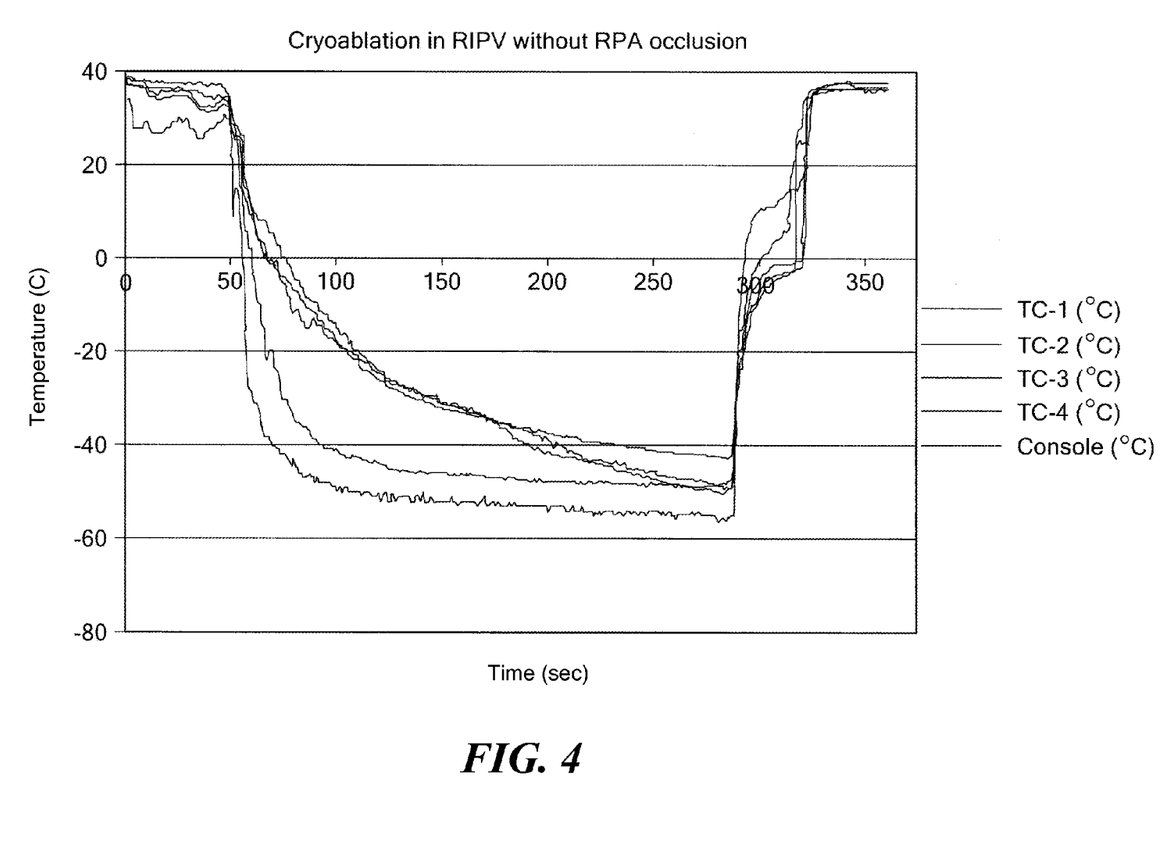
FIG. 4 is a graph of measured temperatures during RSPV cryoablation without occluding the pulmonary artery.
Figure 5:
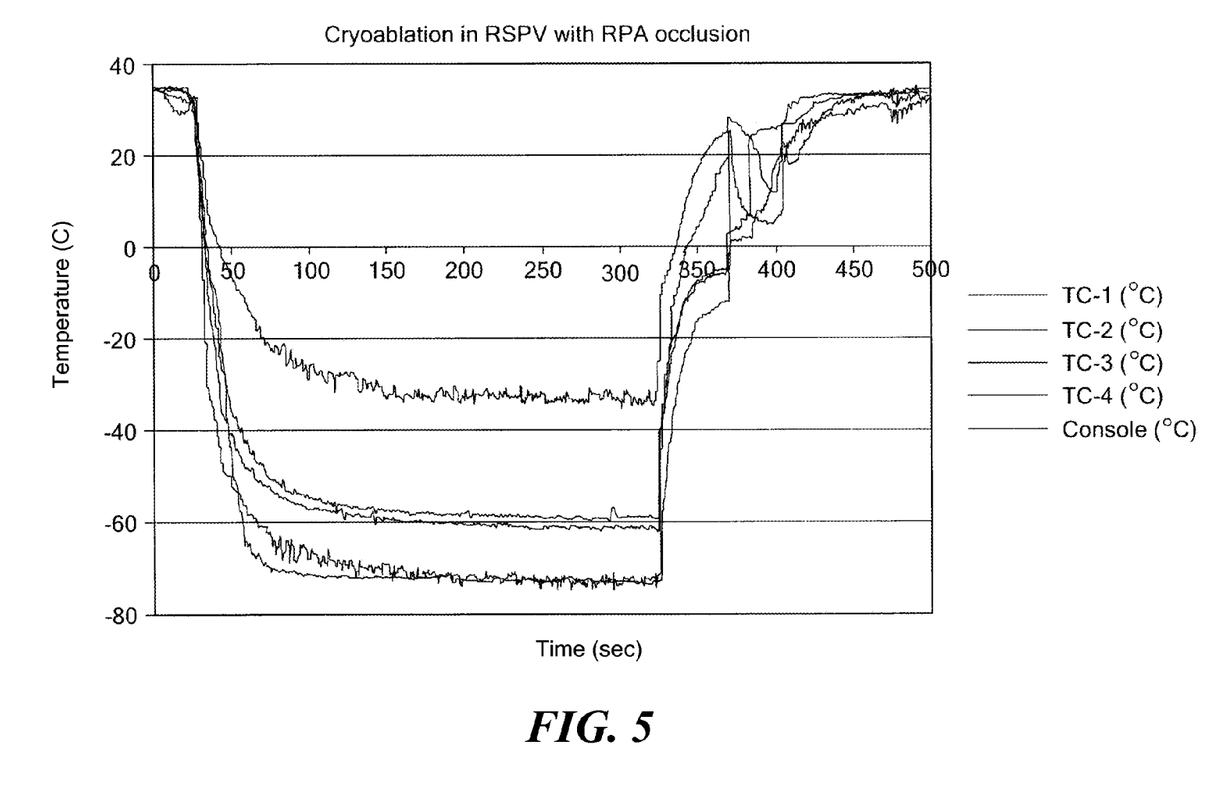
FIG. 5 is a graph of measured temperatures during RSPV cryoablation with occluding the pulmonary artery.

By substantially reducing or eliminating blood flow from the pulmonary vein, and thus the resistive force and thermal load acting on the medical device, a deeper or permanent transmural lesion may be created at the ostium than could otherwise be achieved with conventional methods. Further, because the thermal load associated with the warmer blood flowing past the ablation element has been reduced or eliminated, the cooling power and efficiency of the medical device is greatly increased, i.e., cooler temperatures may be achieved at a faster rate with less coolant needed. FIGS. 4 and 5 include graphical representations of time and temperature for thermal treatment techniques without and with pulmonary artery occlusion, respectively.

In addition to the primary treatment medical device and the secondary occlusion device, a Swan-Ganz catheter (not shown) may be positioned in the pulmonary artery branch not targeted by the occlusion device to allow measurements of pulmonary artery pressure, pulmonary capillary wedge pressure and cardiac output. Furthermore, arterial pressure may be monitored by an arterial line continuously throughout procedure.

Figure 6:
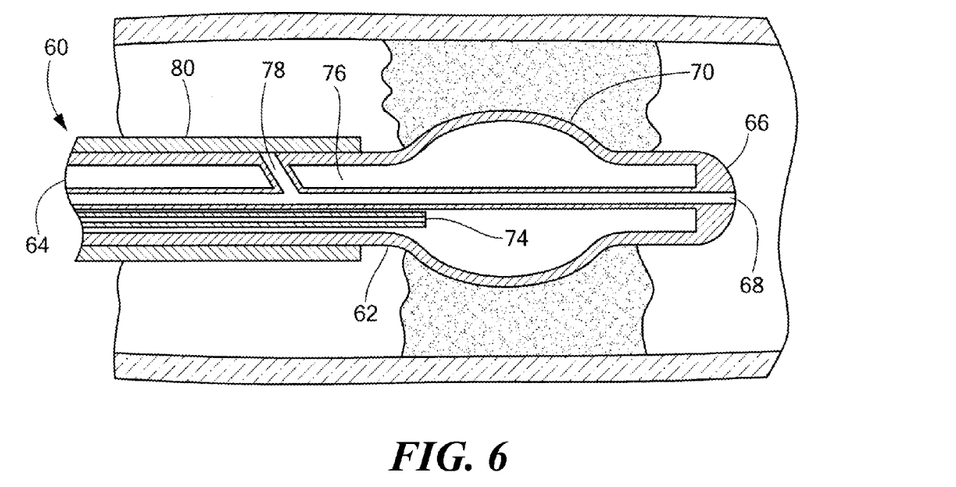
FIG. 6 is an illustration of an embodiment of a medical device in accordance with the principles of the present invention.
Figure 7:
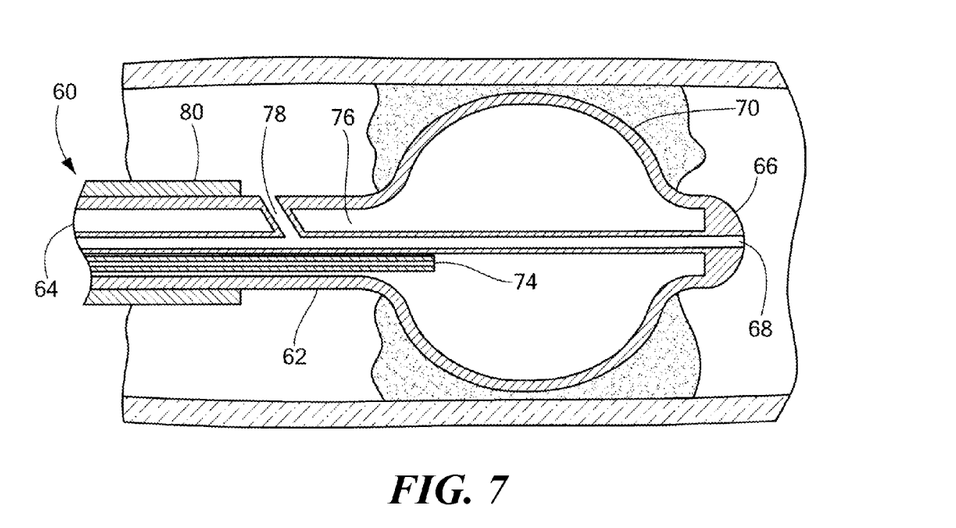
FIG. 7 is an additional illustration of an embodiment of a medical device in accordance with the principles of the present invention.
Figure 8:
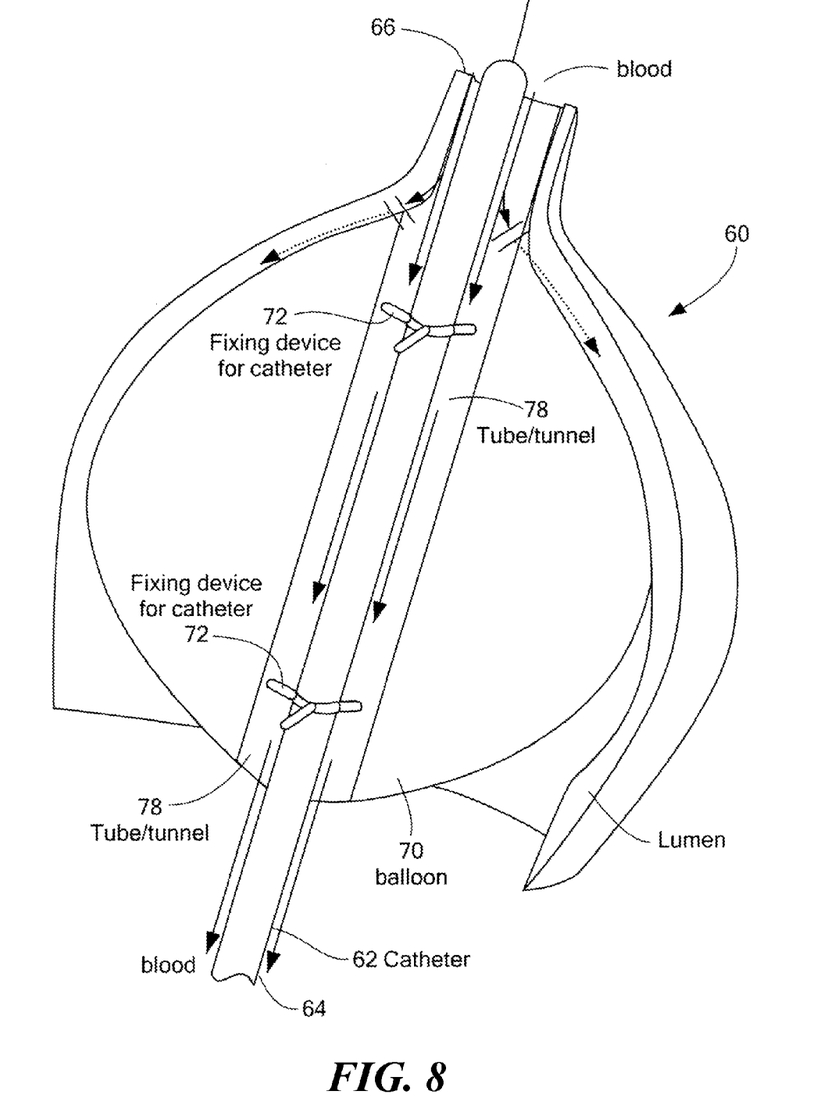
FIG. 8 is another illustration of an embodiment of a medical device in accordance with the principles of the present invention.

Now referring to FIGS. 6-8, the present invention provides a medical device 60 having a flow path through an interior portion of the device in communication with an exterior portion of the device to reduce the resistance experienced from blood or other fluid flow against the surface of the medical device. This flow or bypass path provides an avenue for blood flow to reduce the resistance blood flow would otherwise have on the medical device, such as situations where the medical device is placed in proximity to an orifice or blood flow conduit, such as the pulmonary vein at the left atrium junction.

In particular, the medical device 60 includes an elongate body 62 having a proximal end 64 and a distal end 66, where the elongate body defines a guidewire lumen 68 extending through a substantial length of the device. The medical device 60 further includes a first expandable element 70 disposed on or otherwise coupled to the elongate body 62 at a distal region of the device. One or more spacing elements 72 may be disposed between the balloon/catheter body and the guidewire or guidewire lumen to increase the diameter of the guidewire lumen in the device, as shown in FIG. 8.

An inflation lumen 74 is further included, where the inflation lumen 74 is disposed within the elongate body 62 and is in fluid communication with the first expandable element 70. Moreover, the medical device 60 can include an exhaust lumen 76 disposed within the elongate body which is also in fluid communication with the first expandable element 70. The inflation and exhaust lumens may be oriented in various configurations to achieve fluid communication with the first expandable element while maintaining desired operational characteristics of the device, including uniform fluid dispersion, thermal gradients, fluid flow, or device flexibility. For example, the inflation and exhaust lumens may be coaxial with one another, as well as coaxial with the guidewire lumen. Alternatively, the lumens may be adjacent to one another along a portion of the length of the catheter, or the inflation lumen may be coiled about a portion of either the guidewire lumen or the exhaust lumen, or both.

The medical device 60 of the present invention can further include a bypass path 78, i.e., a path able to direct fluid from a distal region of the first expandable element 70 to a region proximal to the first expandable element 70. The bypass path 78 may include a bypass lumen disposed within a portion of the elongate body, where the bypass lumen may be in fluid communication with the exterior environment of the medical device at both the proximal and distal portions of the bypass lumen, and may include one or more openings in the elongate body for fluid communication. In particular, the bypass lumen 78 may be in fluid communication with the guidewire lumen 68, and may also be coaxial to the guidewire lumen 68 as provided by one or more spacing elements shown in FIG. 8. The bypass lumen 78 may be positioned proximally to the first expandable element 70, where the bypass lumen is in fluid communication with the exterior environment of the elongate body 62, and further in fluid communication with the guidewire lumen 68, thereby creating a fluid path traveling through a portion of the device. Additionally, the bypass lumen 78 may extend from a region proximal of the first expandable element to a region distally of the first expandable element.

A fluid control element 80 may also be included with the medical device 60 in order to selectively control or otherwise manipulate fluid flow through the bypass path 78. For example, the fluid control element 80 may include a guiding catheter or sheath disposed about the elongate body of the medical device, such that the sheath is movably positionable along a length of the elongate body where the bypass lumen is in fluid communication with the exterior environment. As a result, the sheath can be positioned to obstruct the bypass lumen opening in the region proximal to the first expandable element, thereby preventing fluid from entering the bypass lumen. Subsequently, through the use of pull wires or other actuating elements (not shown), or by simply sliding the sheath and/or the elongate body with respect to each other, the sheath can be positioned such that it does not obstruct the bypass lumen, allowing fluid to enter and flow through the bypass lumen to a proximal region of the medical device.

In an exemplary use, the medical device 60 can be used to apply thermal therapy to a selected region of tissue, including the ostium at the pulmonary vein-left atrium junction. For example, the portion of the medical device having the first expandable element can be positioned near the ostium. Once in the desired location, a coolant can be injected into the inflation lumen 74 for delivery into the first expandable element, thereby inflating the first expandable element as well as reducing the temperature of the first expandable element 70. As the first expandable element 70 is inflated, an outer surface of the expandable element 70 will contact the surface of the pulmonary vein or left atrium. Subsequently, the coolant can be continuously circulated through the inflation lumen, first expandable element, and the exhaust lumen, thereby reducing the temperature of the medical device and directly cooling tissue in contact with the expandable element as well as thermally affecting tissue in the surrounding area.

Moreover, the bypass path 78 may be activated, for example, by manipulating the sheath to allow fluid to flow into the bypass lumen and towards the region distally of the obstruction. Alternatively, in the absence of a sheath or other fluid control element and where the bypass path 78 includes the guidewire lumen 68, a guidewire may be either extended or retracted within the guidewire lumen to manipulate at least in part the fluid flowing through the bypass path and/or guidewire lumen. Of course, where a passive bypass path 78 is provided (e.g., no moving or selectively manipulable components are included), simply positioning the medical device in an area of fluid or blood flow will allow the fluid or blood to pass through the bypass path/guidewire lumen of the medical device. As the blood flows through the bypass path 78 of the medical device, the resistive force of the blood flow against the expandable element or medical device will be reduced, allowing for improved stability in positioning the device into contact with the tissue. As a result, better contact may be attained, and increasingly effective thermal treatment may be delivered. Moreover, a portion of the bypass path and/or guidewire lumen may be insulated from the thermal treatment components of the medical device, such as the expandable element, to reduce the warming effect the blood flowing past and/or through the medical device has on the reduced temperature regions of the device.

For thermally or cryogenically treating tissue, the initial phase of the freezing process is a determinant for lesion formation. In particular, the maximal temperature as well as the speed of the temperature drop affects the depth of the necrosis of the lesion induced or created by the thermal treatment. Lesion depth is a central parameter in determining whether a lesion will be transmural and thus permanent or whether the lesion quality fails to include permanent transmurality, and therefore would be susceptible to the recovery of electrical conduction over time. As discussed throughout, the resistive and warming forces of blood flow exiting the pulmonary vein into the left atrium undermines the ability to create the desired rapid cooling and optimal low temperatures for transmural lesions at the pulmonary vein-left atrium junction with a thermal or cryogenic device.

A reduction of blood flow out of the pulmonary veins into the left atrium would occur during a standstill or reduction of the left ventricle contraction or function. When the left ventricle is not contracting or directing blood flow out of the left atrium and towards the aorta, blood flow from the pulmonary vein into the left atrium is reduced. The resulting reduced blood flow would again allow for improved contact and thermal treatment of the pulmonary vein/left atrium tissue. The reduced left ventricle function may be achieved by the application or administration of one or more pharmacological compounds, such as adenosine. Left ventricle function may also be reduced by electrical intervention such as rapid right ventricular pacing. In particular, a rapid right ventricular pacing around approximately 200 beats per minute may be sufficient to cause a mechanical standstill of the heart, thereby reducing blood flow through the pulmonary veins. The mechanical standstill may be performed for a short duration of time in order to achieve the desired thermal treatment results, such as between approximately 30 to 45 seconds, for example.

Figure 9:
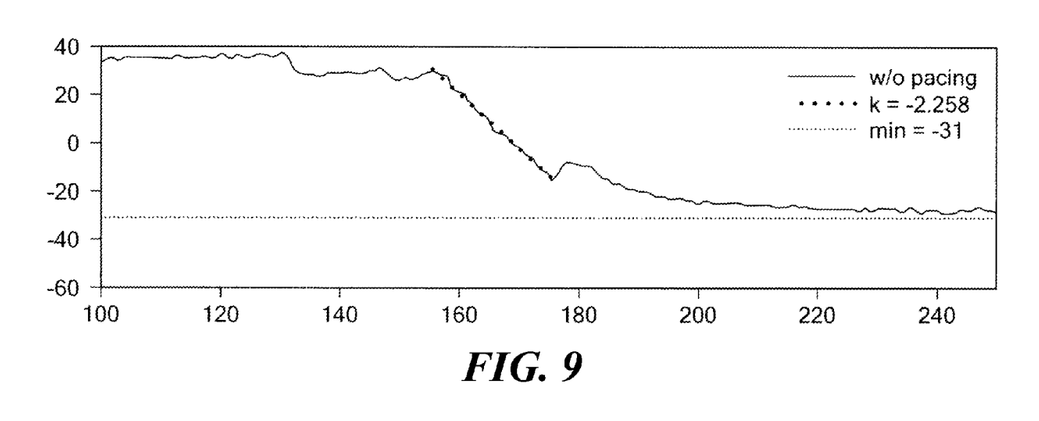
FIG. 9 is a graph of temperature versus time for a thermal therapy technique without electrical cardiac pacing.
Figure 10:
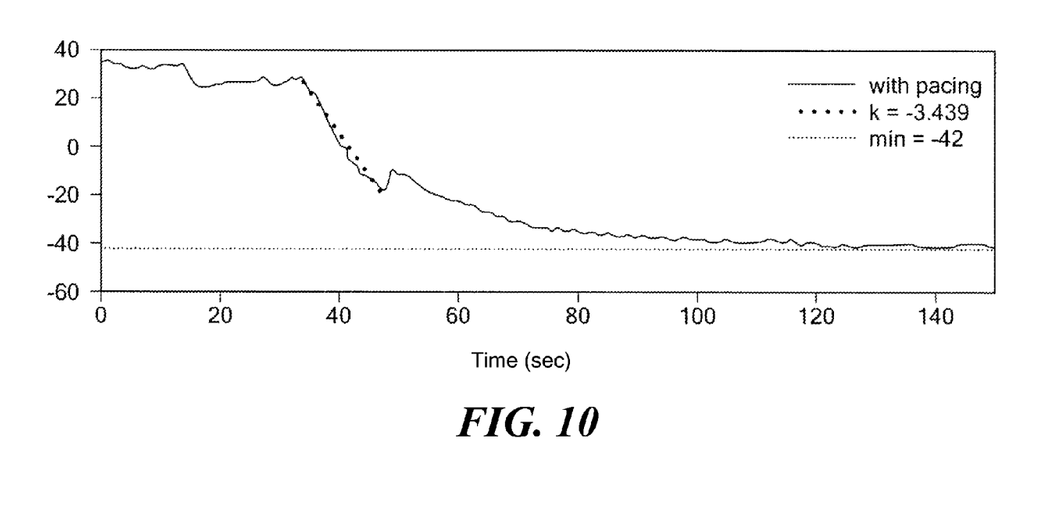
FIG. 10 is a graph of temperature versus time for a thermal therapy technique with electrical cardiac pacing.

Upon inducing a mechanical standstill of the heart, including a reduction of the ventricular function by either the electrical or pharmacological intervention, thermal therapy may be applied with the medical device as described herein. In particular, the balloon, expandable element or similar ablation element may be positioned to contact the target tissue, such as a portion of a pulmonary vein. A coolant may then be delivered to the medical device tip to reduce the temperature of the device and consequently the tissue contacting the device. Due to the reduction in pulmonary vein blood flow, an increased rate of cooling and lower temperatures may be provided, resulting in higher quality lesion formation and thus more effective treatment. FIGS. 9 and 10 include graphical representations of time and temperature for thermal treatment techniques without and with cardiac pacing, respectively.

By providing for the improved isolation of the pulmonary vein for subsequent thermal treatment, better contact between pulmonary vein tissue and the treatment or ablation element is achieved by eliminating or reducing the force of blood flow pushing on the balloon. Further benefits may also include the complete and permanent electrical isolation of the pulmonary veins from the left atrium, deeper lesions within the pulmonary vein ostium ensuring complete electrical isolation, and more uniform lesions around the pulmonary vein ostium. In addition, the thermal efficiencies and efficacies of a cryogenic ablation device are improved, including the achievement of lower temperatures attained during ablation, more uniform temperature distribution over the balloon circumference, improved rate of cooling, leading to a more effective ablation, reduced ablation time compared to ablation without occlusion or isolation, and better visualization of heart/lung anatomy and blood circulation from the pulmonary artery to the pulmonary vein ostium using fluoroscopy and a contrast agent.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method for treating cardiac tissue, comprising:
substantially occluding at least a portion of a pulmonary artery with a first medical device to prevent blood flow into the left atrium of a heart; and
thermally treating an ostium of a pulmonary vein with a second medical device while the at least a portion of the pulmonary artery is substantially occluded by the first medical device, the second medical device including an expandable element and a bypass flow path from a region distal of the expandable element to a region proximal of the expandable element, and a fluid control element surrounding at least a portion of an external surface of the second medical device, the expandable element surrounding at least a portion of the bypass path and longitudinal movement of the fluid control element selectively preventing or allowing fluid flow through the bypass path.

2. The method of claim 1, wherein thermally treating the ostium of the pulmonary vein is accomplished at least in part by cryogenically cooling the ostium of the pulmonary vein.

3. The method of claim 1, wherein the expandable element is a balloon.

4. The method of claim 1, further comprising measuring at least one of a pulmonary artery pressure, a pulmonary capillary wedge pressure and a cardiac output.

5. A method for treating cardiac tissue, comprising:
positioning an expandable element of a first medical device in proximity to an ostium of a pulmonary vein;
expanding the expandable element;
providing a bypass flow path from a region distally of the expandable element to a region proximally of the expandable element, wherein the expandable element surrounds at least a portion of the bypass path;
providing a fluid control element in fluid communication with the bypass flow path, the fluid control element including a sheath surrounding at least a portion of an external surface of the bypass flow path and being transitionable from a first configuration in which at least a portion of the bypass flow path is obstructed by the sheath and a second configuration in which the bypass flow path is unobstructed by the sheath;
selectively obstructing or allowing fluid flow through the bypass flow path by transitioning the sheath externally to the bypass flow path between the first and second configurations while the expandable element is expanded;
thermally treating the ostium of the pulmonary vein with the first medical device; and
substantially occluding a pulmonary artery with a second medical device to prevent blood flow into the left atrium of a heart while the ostium of the pulmonary vein is thermally treated with the first medical device.

6. The method according to claim 5, wherein thermally treating the ostium of the pulmonary vein includes injecting a coolant into the expandable element.

7. The method according to claim 5, wherein the bypass flow path includes at least a portion of a guidewire lumen.

* * * * *